(12) United States Patent
Hellwege et al.

(10) Patent No.: US 7,959,962 B2
(45) Date of Patent: Jun. 14, 2011

(54) LONG-CHAIN INULIN

(75) Inventors: Elke Hellwege, Berlin (DE); Roger Peeters, CH Weert (NL); Jens Pilling, Berlin (DE)

(73) Assignee: Bayer CropScience AG, Monheim am Rhein (DE)

( * ) Notice: Subject to any disclaimer, the term of this patent is extended or adjusted under 35 U.S.C. 154(b) by 765 days.

(21) Appl. No.: 11/911,494

(22) PCT Filed: Apr. 12, 2006

(86) PCT No.: PCT/EP2006/003538
§ 371 (c)(1),
(2), (4) Date: Oct. 12, 2007

(87) PCT Pub. No.: WO2006/108697
PCT Pub. Date: Oct. 19, 2006

(65) Prior Publication Data
US 2008/0255249 A1    Oct. 16, 2008

Related U.S. Application Data

(60) Provisional application No. 60/672,315, filed on Apr. 18, 2005, provisional application No. 60/717,577, filed on Sep. 15, 2005.

(30) Foreign Application Priority Data

Apr. 15, 2005 (EP) .................................. 05090107
Sep. 15, 2005 (EP) .................................. 05090258
Mar. 14, 2006 (EP) .................................. 06075613

(51) Int. Cl.
*A21D 10/00* (2006.01)
*A23L 1/09* (2006.01)
*A23G 3/34* (2006.01)
*A61K 47/26* (2006.01)

(52) U.S. Cl. ......... 426/549; 426/648; 426/658; 424/439

(58) Field of Classification Search ................. 426/549, 426/648, 658; 424/439
See application file for complete search history.

(56) References Cited

U.S. PATENT DOCUMENTS

| 4,758,515 | A | * | 7/1988 | Barwald et al. ............... 435/99 |
| 4,954,622 | A |   | 9/1990 | Cooper et al. |
| 5,846,592 | A | * | 12/1998 | Alderliesten et al. ......... 426/602 |
| 5,958,497 | A | * | 9/1999 | Grimm et al. ................ 426/596 |
| 6,149,965 | A | * | 11/2000 | van Lengerich et al. ..... 426/620 |
| 6,203,797 | B1 | * | 3/2001 | Perry ........................ 424/93.45 |
| 2002/0028928 | A1 |   | 3/2002 | Smits et al. |

FOREIGN PATENT DOCUMENTS

| EP | 0 787 745 A |   | 8/1997 |
| FR | 2851425 A |   | 8/2004 |
| ZA | 9306800 A | * | 5/1995 |

OTHER PUBLICATIONS

Galinsky et al. ["Basic Pharmacokinetics and Pharmacodynamics." in: Remington: The Science and Practice of Pharmacy (Baltimore, Lippincott Williams & Wilkins, 2006), p. 1171].*

Hellwege, et al. (Jul. 18, 2000) "Transgenic potato (*solanum tuberosum*) tubers synthesize the full spectrum of insulin molecules naturally occurring in glove artichoke (*cynara scolymus*) roots" *Proceedings of the National Academy of Sciences of U.S.A.* 97(15): 8699-8704.

Praznik and Beck (1985) "Application of gel permeation chromatography systems to the determination of the molecular weight of inulin." *Journal of Chromatography*, 348:187-197.

Lopez-Molina, et al.(2005) "Molecular properties and prebiotic effect of inulin obtained from artichoke (*Cynara scolymus* L.)." *Phytochemistry*, 66: 1476-1484.

Cooper and Carter (1986) "Anti-complementary action of polymorphic 'solubility forms' of particulate inulin." *Molecular Immunology*, 23(8): 895-901.

* cited by examiner

*Primary Examiner* — Phyllis G. Spivack
*Assistant Examiner* — Nelson C Blakely, III
(74) *Attorney, Agent, or Firm* — Hunton & Williams LLP (57) ABSTRACT

The invention relates to long-chain inulin and its preparation from artichoke roots, its use in foodstuffs and cosmetic preparations and foodstuffs and cosmetic preparations having the long-chain inulin.

19 Claims, 2 Drawing Sheets

LONG-CHAIN INULIN

CROSS-REFERENCE TO RELATED APPLICATIONS

This application is the U.S. National Stage filing of International Application No. PCT/EP2006/003538, filed Apr. 12, 2006, which claims benefit of European Patent Application No. 050 90 107.3, filed Apr. 15, 2005; U.S. Provisional Patent Application No. 60/672,315, filed Apr. 18, 2005; European Patent Application No. 050 90 258.4 filed, Sep. 15, 2005; U.S. Provisional Patent Application No. 60/717,577, filed Sep. 15, 2005; and European Patent Application No. 060 75 613.7, filed Mar. 14, 2006, the disclosures of each of which are hereby incorporated by reference.

BACKGROUND OF THE INVENTION (i) Field of the Invention

The invention relates to long-chain inulin and its preparation from artichoke roots, its use in foodstuffs and cosmetic preparations and foodstuffs and cosmetic preparations comprising the long-chain inulin.

(ii) Description of the Related Art

Inulin is a polysaccharide belonging to the fructan group. It consists of a beta-2-1-linked chain of fructose molecules, this chain having at its end an alpha-D-glucose unit at the reducing end. Inulin occurs in economically recoverable amounts in various plants such as, for example, chicory roots and dahlia tubers. In addition, inulin has been found for example in Jerusalem artichokes and artichokes. The average chain lengths of the various inulins and their physico-chemical properties differ from plant species to plant species.

The extract when inulin is extracted with hot water from the plant tissue comprises, besides the polymeric crude inulin, also monosaccharides such as glucose and fructose, disaccharides such as sucrose and fructooligosaccharides (DP 3-10). These byproducts (mono- and disaccharides, fructooligosaccharides (DP 3-10) may interfere with further processing of inulin. For example, mono- and disaccharides are undesired in the manufacture of dietetic food products. The sweet taste of the mono- and disaccharides, fructooligosaccharides (DP 3-10) interferes with certain applications in the food product sector. Fructooligosaccharides (DP 3-10) may, because of their hygroscopicity and tackiness, interfere greatly in the use of crude inulin in food products both during processing and during storage. On further processing of crude inulin, for example by chemical derivatization, mono- and disaccharides, fructooligosaccharides (DP 3-10) may lead to undefined mixtures of products whose purification is impossible or possible only by costly methods.

It is therefore desirable to provide inulin which, compared with crude inulin, has a low content of mono- and disaccharides and of fructooligosaccharides (DP 3-10).

SUMMARY OF THE INVENTION

The present invention is therefore based on the object of providing inulin with novel properties.

This object is achieved by the provision of the embodiments identified in the claims.

The present invention relates to inulin having an average degree of polymerization $DP_w$ of between 54 and 61, preferably between 55 and 60, particularly preferably between 56 and 57.

DETAILED DESCRIPTION OF THE INVENTION

In this connection and in connection with the present invention, the term "between" is also intended to include the respectively indicated numerical limits.

The term "inulin" is intended to mean in connection with the present invention a polyfructan which consists of a beta-2-1-linked chain of fructose molecules. This chain preferably has at its end a reducing alpha-D-glucose unit. The degree of branching at beta-2,6-linked fructose units is less than 5%, preferably less than 2%.

In connection with the present invention, the term "average degree of polymerization $DP_w$" (mean DP weight) means the quotient of the weight-average molecular mass $M_w$ and the molecular mass of the monomer $M_o$. The weight-average molecular mass $M_w$ results from $$M_w = \frac{\sum N_i M_i^2}{\sum N_i M_i},$$

where Ni is the number of molecules with molecular mass Mi.

The "average degree of polymerization $DP_w$" is preferably measured in connection with the present invention by the method of "gel permeation chromatography with light scattering and refractive index detection (GPC-RI-MALLS system)" described hereinafter.

The inulin of the invention exhibits, by comparison with inulins described in the prior art, the surprising advantage that it can be processed to creams which exhibit unusually high stability on heat treatment or acid treatment, so that they are more suitable for example for particular industrial applications or applications in the cosmetics and/or food products industries. In addition, creams comprising the inulin of the invention show an unexpectedly high stability toward shear forces. The inulin of the invention thus exhibits the further advantage, compared with conventional inulin, that it can be processed better in industrial processes in which strong shear forces act.

Furthermore, the inulin of the invention excels in outstanding beneficial viscosity properties and high gel strength.

The inulin of the invention also shows a slower fermentation in comparison to so far employed products which is beneficial in prophylaxis of diseases in the distal colon.

Moreover, the inulin of the invention shows a stronger prebiotic effect in comparison to so far employed products. Particularly, inulin of the invention stimulates the generation of bifidobacteria in advantageous manner with simultaneous reduction of undesired and/or pathogenic bacteria. Therefore, inulin of the invention is suitable for use in foodstuff and/or medicaments for prevention and treatment of intestinal dysfunctions and diseases, particularly in the distal colon.

Finally, inulin of the invention also imparts beneficial usage properties to several foodstuffs as for example viscosity building, emulgation capability, water binding capacity and crumb formation.

In a further embodiment, the inulin of the invention has a content of fructooligosaccharides (oligofructans) having a DP of from 3 to 10 is less than 3%, preferably less than 1.5%, particularly preferably less than 0.7%, very particularly preferably less than 0.3%.

The content of fructooligosaccharides having a DP of from 3 to 10 is measured in connection with the present invention by the method described below (see general methods: "Analysis of inulin by ion exchange chromatography and with pulsed amperometric detection (HPAEC-PAD) and "Determination of the percentage content of inulin oligomers with a chain length from DP=3 to DP=10 in the total inulin by HPAEC-PAD").

In a further embodiment, the inulin of the invention has a glucose content of less than 2%, preferably less than 1%, particularly preferably less than 0.5%, very particularly preferably less than 0.2%.

In a further embodiment, the inulin of the invention has a fructose content of less than 2.5%, preferably less than 1.5%, particularly preferably less than 1.0%, very particularly preferably less than 0.3%.

In a further embodiment, the inulin of the invention has a sucrose content of less than 2%, preferably less than 1%, particularly preferably less than 0.5%, very particularly preferably less than 0.3%.

In a particularly advantageous embodiment of inulin of the invention for food applications the fraction of mono- and disaccharides is less than 0.5%.

Unless otherwise stated, all percentages are weight percent based on the total dry mixture of inulin and other substances.

The content of fructose, glucose and sucrose is measured in connection with the present invention by the optical enzymatic method described below (general methods: "sugar determination").

In a further embodiment, the inulin of the invention has a weight-average molecular mass $M_w$ of between 8740 g/mol and 9890 g/mol, preferably between 8910 g/mol and 9720 g/mol, particularly preferably between 8910 g/mol and 9250 g/mol.

The weight-average molecular mass $M_w$ is preferably measured in connection with the present invention by the method of "gel permeation chromatography with light scattering and refractive index detection (GPC-RI-MALLS system)" described hereinafter.

In a further embodiment, the inulin of the invention has an average degree of polymerization $DP_{n\ (GPC)}$ of between 44 and 48, preferably between 45 and 48, particularly preferably between 46 and 48, as measured with gel permeation chromatography (GPC).

The "average degree of polymerization $DP_n$" is measured in connection with the present invention preferably by the method of "gel permeation chromatography with light scattering and refractive index detection (GPC-RI-MALLS system)" described hereinafter.

In connection with the present invention, the term "average degree of polymerization $DP_n$" (mean DP number) means the quotient of the number-average molecular mass $M_n$ and the molecular mass of the bound monomer $M_o$ (anhydrofructose=162 g/mol). The number-average molecular mass $M_n$ results from $$M_n = \frac{\sum N_i M_i}{\sum N_i},$$

where $N_i$ is the number of molecules having molecular mass $M_i$.

In a further embodiment, the inulin of the invention has a molecular weight distribution of from 1620 g/mol to 40 000 g/mol, preferably from 2268 g/mol to 32 000 g/mol, particularly preferably from 2592 g/mol to 29 160 g/mol.

The molecular weight distribution is preferably measured in connection with the present invention by the method of "gel permeation chromatography with light scattering and refractive index detection (GPC-RI-MALLS system)" described hereinafter.

It is also possible to determine the mean degree of polymerization $DP_n$ by the method of acidic hydrolysis with perchloro acetic acid (PCA, identical to trichloro acetic acid—TCA). When applying this method, a mean degree of polymerisation DPn (PCA) of between 48 and 56, preferably between 48 and 52, is obtained for inulin of the invention. The method of hydrolysis with PCA is carried out as described in the examples below.

A further object of the invention is an aqueous paste made from inulin of the invention, obtainable by dispersing the inulin in water, shearing the obtained dispersion to homogeneity, storing the thus obtained product for 12-24 h at 4-15° C. and stirring it to a homogeneous paste after conditioning to room temperature. A preferred paste contains 5-40 wt %, still more preferably 5-30 wt % and particularly preferably 10-20 wt % inulin, based on the total weight of the paste.

The inulin of the invention shows a surprisingly high acid stability against acid. Particularly, an aqueous paste from inulin of the invention shows a high stability against acid. The increase of viscosity of an aqueous paste of inulin of the invention at pH 4 and room temperature over a storage time of 2 weeks is less than 10% in relation to the initial value of viscosity. Preferably, however, the increase of viscosity is less than 7% and most preferably less than 5%, in relation to the initial value of viscosity, respectively.

The initial value of viscosity is the value that a paste shows after dispersing of the inulin in water, storing for 12-24 h at 4-15° C., conditioning to room temperature and subsequent stirring to a homogeneous, smooth paste. Details concerning the manufacture of the pastes are described in the working examples.

The values of acid stability were measured under following conditions: room temperature, rotational viscometry (Rotovisco VT 550), diagonal blade stirrer, 128 rpm, measuring time 15 min, concentration of inulin in water preferably 10-30% w/v (1% w/v=10 g/liter), especially preferably 15% w/v. A detailed description of the method is given in the examples. Such low increases of viscosity (post thickening) are advantageous in application of inulin in foodstuffs with acidic pH.

Also excellent is the shear stability of an aqueous inulin paste of the invention compared to commercially available products. The viscosity value of an aqueous inulin paste is still more than 85%, preferably more than 90% and most preferably more than 95% of the initial value after 15 min of shear. The paste is obtained as described previously. The values of shear stability are determined under following conditions: room temperature, rotational viscometry (Rotovisco VT 550), diagonal blade stirrer, 128 rpm, measuring time 15 min, concentration of inulin in water preferably 15% w/v (1% w/v=10 g/liter). A detailed description of the method is given in the examples. High shear stability is advantageous in the manufacture of food- and cosmetic preparations, particularly when processed under stirring.

Compared to other commercially available inulins the inulin of the invention stands out at surprisingly high gel strength. At a concentration of 20-50% (w/v) of inulin in water gel strengths of 30-100 N, more advantageously 40-100 N and most advantageously 50-100 N are obtained when inulin is dissolved at 90° C. and subsequently cooled down to room temperature over a period of 20 h. The thus obtained gels have a particle like character (particle gels). The measuring method for determination of gel strength is described in detail in the working examples.

Moreover, inulins of the invention show surprising viscosity properties in dissolved state in water. At a concentration of 30% w/v inulin in water at a measuring temperature of 90° C.

and a shear rate of 20 s$^{-1}$ (CVO 120HR Bohlin/Malvern rheometer, cone-plate geometry) a viscosity of 300-1000 mPas, preferably 400-1000 mPas, still more preferably 500-1000 mPas is achieved. For details of the measuring method it is referred to the method description in attached examples. These values are higher as could be expected in comparison with so far known inulins. Such high viscosity values at relatively low concentrations are especially beneficial in food applications.

In addition to the previously described inulin the invention is also directed to compositions containing the previously described inulin of the invention as well as one or more edible or pharmaceutically acceptable components. Typical compositions comprise food for human and animals, drinks, functional foods, medicaments and pharmaceutical compositions (including prophylactic compositions and therapeutic compositions), and intermediates thereof.

By functional food according to the present invention is meant food containing, beyond the traditional nutrients, an ingredient that may provide a health beneficial effect (definition according to the Institute of Medicine of the National Academy of Sciences (USA; 1994).

The mentioned edible or pharmaceutically acceptable components are preferably selected from the group consisting of sugars (for example: glucose, fructose, sucrose, lactose, galactose, maltose, isomaltulose), polyols (for example: sorbitol, lactitol, maltitol, isomalt, mannitol, xylitol), maltodextrins, sweeteners, hydrogenated glucose syrups, food and feed additives, food and feed intermediates, food and feed products, edible liquids, drinks, bio-available sources of minerals, pharmaceutically acceptable excipients, pharmaceutically and therapeutically active substances, pharmaceutical compositions and medicaments.

A particularly preferred composition of the present invention comprises inulin of the invention in the presence of an edible or pharmaceutically acceptable, bio-available source of minerals, particularly a source of calcium and/or magnesium and/or iron, such as for example dairy products and salts and complexes of calcium, magnesium and iron.

As previously stated, the objective of the present invention was to provide with an inulin having outstanding beneficial properties for use in foods, wherein the terms foods and foodstuffs according to the present invention are equivalent. In a further aspect the present invention therefore is also directed to foods and dietary supplements comprising the previously described inulin. The term food embraces according to the present invention food for humans as well as food for animals and feed, respectively. Dietary supplements embrace dietary supplements for humans and animals.

In particular preferably, a food is selected from dairy, yogurts, ice creams, dairy based smoothies, dairy toppings, puddings, milk shakes, custards, cheeses, nutritional bars, energy bars, breakfast bars, confection, bakery, crackers, cookies, biscuits, grain chips, trail mix, iced tea mix, fruit juice smoothies, weight management drinks, ready to drink beverages, sports drinks, endurance drinks, supplement powdered drink mixes, infant and baby formula, calcium fortified orange juice, bread, croissants, cereals, pastas, bread spreads, sugar free candies and chocolates, calcium candy chews, meat products, mayonnaise, salad dressings, nut butters, frozen entrees, sauces, soups and ready meals.

In one embodiment of the invention, the food is a food made by an extrusion process, as for example a cereal.

In a further aspect the present invention is directed to cosmetic preparations comprising the previously described inulin. Particularly preferably the cosmetic preparation is a creme, particularly cremes for skin and face.

In a further aspect the present invention is directed to the use of the previously described inulin as supplement in foods, functional foods and cosmetic preparations. Particularly, the use is also related to all specific foods and cosmetic preparations which are mentioned above.

In still another aspect, the present invention is directed to the use of inulin of the invention for the preparation of a pharmaceutical composition or a medicament.

Inulin of the invention is beneficially usable in foods, functional foods, pharmaceutical compositions or medicaments for modifying or modulating the bacterial flora composition in the colon, especially in the distal part of the colon, of humans, mammals or other vertebrates.

Inulin of the invention can also be used in foods, functional foods, pharmaceutical compositions or medicaments for modifying or modulating the fermentation pattern of inulin in the colon, especially in the distal part of the colon, of humans, mammals or other vertebrates Finally, inulin of the invention can be used in foods, functional foods, pharmaceutical compositions or medicaments, which have the following beneficial effects: dietary fibre effects, modulation of gut function, prebiotic action and/or bifidogenicity, increased absorption of minerals, as for example calcium, magnesium and iron, bone mineral density increase, bone mineral content increase, peak bone mass increase, improvement of the bone structure, reduction of bone mineral density loss, reduction of loss of bone structure, modulation of lipid metabolism, stimulation of the immune system, prevention of cancer and reduction of the risk of cancer, prevention of colon cancer and reduction of the risk of colon cancer and prevention of breast cancer.

Below, the invention is illustrated by means of examples which are not intended to be a limitation of the general inventive concept.

EXAMPLES

General Methods

1. Inulin Purification and Fractionation 1 kg of roots with a root diameter of 0.5-5.0 cm from artichoke plants about 1 year old are used for the preparation. This material is homogenized in 200 g portions in a homogenizer (Waring Blender, from VWR International GmbH, Darmstadt, Germany) with 500 ml of water at 85° C. The resulting homogenates are combined in a metal vessel standing in a water bath at 85° C., the extraction volume is increased to 5 l of water, and the inulin is extracted from the material by stirring at 80-85° C. for 45 minutes. The hot extract is filtered through a 125 μm sieve. The filter cake is transferred into a cotton cloth and squeezed out. The squeezed-out solution is combined with the filtrate (total about 5 liters).

The crude inulin extract is purified to remove non-saccharides by liming and carbonation. In the preliming, the crude extract is adjusted to a pH of 11.2 by stirring with $Ca(OH)_2$. The extract remains at this pH for 30 minutes, the temperature of the extract being 65° C. For the main liming, the pH is raised to pH>12 by adding $Ca(OH)_2$, and the extract is then stirred at 85° C. for 30-45 minutes. In order to make the precipitated turbid matter more easily filterable, the pH of the extract is reduced to pH=10.8 in a first carbonation step by quickly passing in $CO_2$. The temperature during this step is about 65° C. The sludge which forms is removed by centrifugation (2800 g, 10 min). In a second carbonation step, the pH of the supernatant is reduced to pH=8.9 by passing in $CO_2$. The sludge which forms is removed from the extract by centrifugation (2800 g, 10 min) and subsequent filtration through a paper filter (Schleicher& Schuell, order No. 10311614) using a suction funnel under vacuum.

The extract is decolorized by gradual addition of 10-15% (w/v) ion exchanger (mixed bed resin TMD8, Sigma, order No. M8157) while stirring in a batch process. After removal of the ion exchanger by filtration through 30 μm sieves, the solution is adjusted to pH=7.0 with KOH. For selective concentration of longer-chain inulin polymers (DP>10), absolute ethanol is added to the solution until the final concentration is 40% (v/v), and the solution is thoroughly mixed and incubated at 8° C. overnight. The precipitated inulin is sedimented by centrifugation (2800 g, 10 min). The inulin precipitate is washed twice with 1.6 liters of 80% (v/v) ethanol. The washed inulin is dissolved in 1 liter of water in a water bath at 95° C., suspended matter is removed by filtration through a 30 μm sieve, and the inulin solution is frozen at −80° C. The water is then removed by freeze drying (Alpha 1-4, from Christ, Germany), and the dried inulin powder is isolated.

2. Fructan Determination 2.1 Fructan Assay Procedure

The fructan content of a sample can be determined using the "Fructan Assay Procedure" kit (from Megazyme International Ireland Ltd, Wicklow, Ireland). The principle of this assay is based on hydrolysis of the fructan to its reducing monomers glucose and fructose and subsequent photometric determination (wavelength=410 nm) of the content of these reducing sugars (glucose, fructose) after color formation by the so-called "PAHBAH method" (see below for details of the method).

In a first step, the sucrose present in the extract is hydrolyzed by the specific enzyme sucrase to glucose and fructose. In addition, starches and maltodextrins present in the extract are likewise degraded to glucose with a mixture of the highly purified enzymes β-amylase, pullulanase and maltase. The resulting reducing sugars are then reduced to sugar alcohols by treatment with alkaline borohydride solution and thus removed from the solution. Addition of dilute acetic acid neutralizes the solution and removes excess borohydride. The fructan is then hydrolyzed with purified fructanase (exo-inulinase) to fructose and glucose, and the content of the resulting monosaccharides is determined by the PAHBAH method.

Chemicals and Solutions in the "Fructan Assay Procedure" Kits 1. 50 U of sucrase (yeast), 500 U of β-amylase (*B. cereus*), 100 U of pullulanase (*K. pneumoniae*) and 1000 U of maltase (yeast) are contained as a freeze-dried powder and are dissolved in 22 ml of 0.1 M sodium maleate buffer of pH 6.5 (referred to as "enzyme 1" hereinafter) for the measurement.
2. 8000 U of fructanase (exo-inulinase) are contained as a freeze-dried powder and are dissolved in 22 ml of 0.1 M sodium acetate buffer of pH 4.5 (referred to as "enzyme 2" hereinafter) for the measurement.
3. Standard fructose solution (1.5 mg of fructose/ml) dissolved in 0.2% benzoic acid.
4. Fructan control powder
   Dahlia fructan with a known fructan content, freeze-dried in the presence of alpha-cellulose.

Solutions Not Present in the Kit:

I. PAHBAH reagent
   Solution A: 10 g of PAHBAH (ρ-hydroxybenzoic acid hydrazide, Sigma order No. H-9882) are added to 60 ml of distilled water in a 250 ml glass beaker, and 10 ml of concentrated hydrochloric acid are added to the suspension while stirring. The solution is made up to 200 ml and stored at room temperature.

Solution B: While stirring, firstly 24.9 g of trisodium citrate and then 2.20 g of calcium chloride and finally 40 g of sodium hydroxide are dissolved stepwise in 500 ml of distilled water. After the addition of sodium hydroxide, the solution may be milky, but becomes clear when the solution is made up to 2 l with water. The solution is stored at room temperature.

Shortly before use, 20 ml of solution A are added to 180 ml of solution B and thoroughly mixed (=PAHBAH reagent). The solution must be stored on ice and can be used for 4 hours.

II. 50 mM sodium hydroxide solution

III. Alkaline sodium borohydride solution
   10 mg/ml sodium borohydride (Sigma, order No. S-9125) in 50 mM sodium hydroxide IV. 100 mM acetic acid Detection Method:

1. (A) Fructan control
   20 mg of the fructan control powder are extracted in 1 ml of double-distilled water in a heating block at 95° C. for 30 minutes. After centrifugation (13 000×g for 5 minutes), the supernatant is transferred into a new reaction vessel, and the precipitate is again taken up in 1 ml of distilled water and extracted in the heating block at 95° C. for 30 minutes. After renewed centrifugation (see above), the supernatant is removed and combined with the first supernatant.

(B) Purified fructan/inulin
   20 mg are extracted in 2 ml of double-distilled water in a heating block at 95° C. for 1 hour. After centrifugation (13 000×g for 5 minutes), the supernatant is transferred into a new reaction vessel and used for the measurement.

2. 200 μl of sample are mixed with 200 μl of enzyme 1 and incubated at 40° C. for 60 minutes (incubation time extended by 30 minutes from the megazyme protocol).
3. 200 μl of alkaline sodium borohydride solution are added, and the solution is thoroughly mixed and incubated at 40° C. for 30 minutes in order to achieve complete conversion of the reducing sugars to sugar alcohols.
4. The excess borohydride is removed, and the solution is adjusted to pH=4.5, by adding 500 μl of 100 mM acetic acid and thoroughly mixing.
5. The extracts from the purified fructan/inulin—not the fructan control—are diluted 1:5 with double-distilled water. Then, 100 μl of solution from this mixture and from the fructan control are mixed with 100 μl of 100 mM Na acetate buffer of pH 4.5.
6. The 200 μl solutions are mixed with 100 μl of enzyme-2 and incubated at 40° C. for 60 minutes (incubation time extended by 40 minutes from the megazyme kit in order to achieve complete hydrolysis of the fructan).
7. A fructose standard is included as further sample. 200 μl of the standard fructose solution present in the kit are treated with 900 μl of 100 mM sodium acetate buffer of pH 4.5 and mixed. 4×200 μl of this mixture are removed and mixed with a further 100 μl of 100 mM sodium acetate buffer of pH 4.5.
8. All the samples and an additional blank sample (300 μl of 100 mM sodium acetate buffer of pH 4.5) were mixed with 5 ml of PAHBAH reagent and incubated in a boiling water bath for exactly 6 minutes.
9. The samples are then cooled immediately in cold water (10-15° C.) for about 5 minutes.
10. The absorption of all the solutions is measured in a spectrophotometer at a wavelength of 410 nm against the blank sample.

The calculation takes place according to the following equation:

$$\text{Fructan (\% w/w)} = \Delta E \times F \times 5 \times V_{Ex} \times 1.1/0.2 \times 100/W \times 1/1000 \times 162/180$$

$\Delta E$=the PAHBAH absorption of the samples measured against the blank sample F=the factor for conversion of the fructose absorption into μg of fructose (54.5 μg of fructose/absorption)

5=factor to convert from 200 μl to 1 ml incubation volume $V_{Ex}$=extract volume 1.1/0.2=0.2 ml from 1.1 ml enzymatic digestion W=weight of the extracted sample in mg 100/W=factor to indicate fructan as % of the initial weight (W)

1/1000=conversion of μg into mg

162/180=factor to convert measured free fructose into the anydrofructose bound in the fructan 2.2 Fructan Determination by Hydrolyses with Exoinulinase 1% (w/v) material is extracted in double-distilled water at 95° C. for 30 minutes and then diluted 1:25 with water (see above). For the exo-inulinase digestion (100 μl), 50 μl of extract are incubated in 0.1 M sodium acetate of pH 5.6 with 25 U of exo-inulinase (Megazyme International Ireland Ltd, Wicklow, Ireland, article No. E-EXO1) at 40° C. for three hours. The reaction is stopped by incubation at 95° C. for 10 minutes. The photometric determination of the liberated glucose and fructose takes place as described in the "sugar determination" method. The fructan content is determined by adding the glucose and fructose contents and by including the factor 162/180 with which the measured free hexoses are converted into the hexoses bound in fructan.

3. Sugar Determination (Glucose, Fructose and Sucrose)

The glucose, fructose and sucrose contents were determined by photometry in an enzymatic assay via conversion of NAD$^+$ (nicotinamide adenine dinucleotide) to NADH (reduced nicotinamide adenine dinucleotide). The aromatic character of the nicotinamide ring is lost in the reduction, and thus the absorption spectrum is changed. This change in the absorption spectrum can be detected by photometry.

Glucose and fructose are converted by means of the enzyme hexokinase and adenosine triphosphate (ATP) into glucose 6-phosphate and fructose 6-phosphate. The glucose 6-phosphate is then oxidized by the enzyme glucose-6-phosphate dehydrogenase to 6-phosphogluconate. NAD$^+$ is reduced to NADH in this reaction, and the amount of NADH formed is measured by photometry. The ratio of NADH formed to the glucose present in the extract is 1:1, so that the glucose content can be calculated from the NADH content using the molar extinction coefficient of NADH (6.31 mmol$^{-1}$ cm$^{-1}$) according to Lambert-Beer's law.

After the oxidation of the glucose 6-phosphate is complete, the fructose 6-phosphate which is likewise produced in the solution is converted by the enzyme phosphoglucoisomerase into glucose 6-phosphate, which in turn is oxidized to 6-phosphogluconate. The ratio of fructose and the amount of NADH formed is also 1:1. The fructose content is calculated from the amount of NADH formed, as described for glucose.

Subsequently, the sucrose present in the extract is cleaved by the enzyme sucrase (from Megazyme) into glucose and fructose. The liberated glucose and fructose molecules are then converted by the abovementioned enzymes in the NAD$^+$-dependent reaction into 6-phosphogluconate. Two molecules of NADH are formed in the conversion of one molecule of sucrose into 6-phosphogluconate. The amount of NADH formed is likewise measured by photometry, and the sucrose content is calculated therefrom using the molar extinction coefficient of NADH.

4. Analysis of Molecular Weight Distribution 4.1 Gel Permeation Chromatography with Light Scattering and Refractive Index Detection (GPC-RI-Malls System)

The inulins/fructans are dissolved in water in a concentration of 0.5% (w/v). The solutions are heated at 95° C. for 10 minutes. The polymers are analyzed using the following instruments: PL120 gel chromatograph (from Polymer Laboratories, Germany), Midas Autosampler (from Spark, Holland), DAWN-EOS light scattering detector (Wyatt Technology Santa Barbara, USA) with $\lambda_0$=690 nm and 16 detectors in the range of angles from 14.9 to 162.9° plus K5 flow cell, combined viscosity-refractive index detector $\eta$-1002 (from: WGE Dr. Bures GmbH & Co KG, Germany). The polymers are fractionated on the following columns: TSK precolumn, TSK6000PW, TSK3000PW (from Tosoh BioScience GmbH Stuttgart, Germany). 100 μl of solution were injected. The fractionation took place at a temperature of 30° C. and with a flow rate of 0.8 ml/min with 0.3 M NaNO$_3$ as eluent. The Astra 4.90.08 program (from Wyatt Technology Santa Barbara, USA) analyzes the molecular weight distribution of the samples in the GPC-RI-MALLS-MALLS.

4.2 Determination of DP$_n$ of Inulin with PCA Hydrolysis

Inulin is totally hydrolysed with perchloro acetic acid (PCA). From the ration of generated fructose to generated glucose the number average of chain length (DPn) of the inulin sample can be determined.

Sample Preparation:

50.0+/−5.0 mg Inulin were weighed exactly in a 1 ml flask. For dissolving 700 μl H$_2$O$_{bidest}$ are added. Then, the sample is agitated in order to detach the sample material from the bottom of the vessel as good as possible and subsequently let stand in a boiling water bath (~99° C.). During incubation the flask is agitated every 30 seconds. After incubation the sample is cooled down to room temperature in order to fill it up with H$_2$O$_{bidest}$ till the 1-ml calibration mark. The sample solution has an inulin concentration of 5.0+/−0.5%. For determination of sugar before hydrolysis 200 μl are retained and frozen at −20° C. Before sugar measurement this sample is thawn at room temperature, mixed, dissolved for 5 min under agitation at 1400 rpm in a 95° C. heating block and centrifuged for 2 min at 4000 rpm.

Hydrolysis and Sample Withdrawal:

250 μl of the ~5% inulin solution are given in already prepared 250 μl 18% PCA (end concentration inulin 2.5%, PCA 9%). Alternatively, 900 μl of 5% inulin solution are given in already prepared 100 μl 5% PCA (end concentration inulin 4.5%, PCA 0.5%). The hydrolysis mix is mixed and centrifuged for 1 min at 4000 rpm. Subsequently, the hydrolysis mix is put on a heater (heating block) at 37° C. or, alternatively, 56° C. At different points of time, after mixing the hydrolyzate again and centrifuging for 1 min at 4000 rpm, 100 μl of sample are withdrawn and immediately neutralized by addition of a neutralization mix of aqueous NaOH. The pH value in the neutralized sample is checked with pH-indicator (pH paper). The points of time for withdrawal of sample are at 50 min, 2 h, 3 h and 4 h and 24 h. All neutralized samples were frozen at −20° C. Prior to measurement of sugars, these samples are thawed at room temperature, mixed and centrifuged for 2 min at 4000 rpm. For measurement of fructose a 1:10 dilution is prepared by adding 10 μl neutralized hydrolyzate to 90 μl H$_2$O$_{bidest}$.

Measurement of Sugars

For determination of fructose and glucose liberated during hydrolysis in all samples a photometric glucose- and fructose measurement is done. In the sample before hydrolysis sucrose is also determined besides glucose and fructose. The measurement is done as a repeat determination in micro titer plates by using the SPECTRAmax photometer (Molecular Devices). All employed enzyme solutions are prepared in measuring buffer, consisting of 50 mM imidazole-HCl pH 6.9, 2.5 mM $MgCl_2$, 1 mM ATP and 0.4 mM NADP. The conversion from NADP to NADPH is observed at 340 nm.

For measurement of sugars prior to hydrolysis the undiluted 5% inulin solution is used. 10 µl of this solution are given to 200 µl measuring buffer. The determination of glucose is done by addition of 2 µl of a mixture of hexokinase (from yeast, 0.3 U/µl) and glucose-6-phosphat-dehydrogenase (from yeast, 0.14 U/µl). After complete conversion of glucose 2 µl phosphoglucose-isomerase (from yeast, 0.14 U/µl) are added in order to determine fructose. Once the fructose is converted completely, 2 µl β-Fructosidase (3 U/µl) are added for cleavage of sucrose present.

The measurement of glucose and fructose are done as previously described under item 3 (determination of sugars).
Calculation:

In the calculation, for the conversion of NADP to NADPH a molar extinction coefficient of 6.23 $l*mmol^{-1}*cm^{-1}$ is taken as basis. The concentration of glucose and fructose, which is already present prior to hydrolysis, is subtracted from the concentrations of glucose and fructose in the hydrolyzates. Likewise, glucose and fructose is subtracted, which would be liberated from hydrolyzed sucrose that is present in the sample prior to hydrolysis. Concentrations of fructose and glucose are thus obtained which are generated during hydrolysis of the inulin. Hence, the number average chain length ($DP_n$) can be calculated according to following formula:

$$DP_n = (c_{Fruktose}/c_{Glukose}) + 1$$

Here, it is assumed that every inulin molecule has a terminal glucose.

For control of completeness of hydrolysis, the rate of recovery can be determined by alluding the generated concentrations of glucose and fructose to the applied mass of inulin.

5. Analysis of Inulins by Ion Exchange Chromatography and with Pulsed Amperometric Detection (HPAEC-PAD)

The inulin polymer mixtures are fractionated by anion exchange chromatography and pulsed amperometric detection on a DIONEX system (GP50 gradient pump, AS50 autosampler, model 585 column oven, ED50 detector, CarboPac PA-100 precolumn, CarboPac PA-100 separating column, from DIONEX Corporation, Germany). The column oven has a temperature of 30° C. Eluent A is 150 mM NaOH, and eluent B is 1 M sodium acetate in 150 mM NaOH. The flow rate is 1 ml/min.

0.5-2% (w/v) inulin solutions are prepared in double-distilled water and incubated at 95° C. until the inulin has completely dissolved.

The wave form on the ED50 detector has the following composition:

| Time (s) | Potential (V) | |
|---|---|---|
| 0.00 | 0.05 | |
| 0.28 | 0.05 | Start of integration |
| 0.48 | 0.05 | End of integration |
| 0.49 | 0.65 | |
| 0.60 | 0.65 | |
| 0.61 | −0.96 | |

| Time (s) | Potential (V) |
|---|---|
| 0.72 | −0.96 |
| 0.73 | 0.05 |

The following gradient is applied for maximal fractionation of the inulin polymers:

| Gradient 1: | Time (min) | Eluent A (%) | Eluent B (%) |
|---|---|---|---|
| (90 min) | 0 | 100 | 0 |
| | 5 | 100 | 0 |
| | 40 | 72 | 28 |
| | 70 | 55 | 45 |
| | 75 | 0 | 100 |
| | 80 | 0 | 100 |
| | 85 | 100 | 0 |
| | 90 | 100 | 0 |

The DIONEX Chromeleon (Version 6.6) software is used to analyze the chromatograms.

6. Determination of the Percentage Content of Inulin Oligomers with Chain Lengths from DP=3 to DP=10 in the Total Inulin by HPAEC-PAD The proportions of inulin polymers with a chain length from DP3 to DP10 are determined by anion exchange chromatography and amperometric detection (see method 6), but with an altered detector setting and with a different salt gradient.

2% (w/v) aqueous solutions are prepared from purified artichoke inulin. 100 µl of this solution are separated in each anion exchange chromatography run with gradient 2, with the ED50 detector disengaged, and the individual oligofructans are collected after the column. Four separate runs are carried out with the 2% strength inulin solution.

| Gradient 2: | Time (min) | Eluent A (%) | Eluent B (%) |
|---|---|---|---|
| (50 min) | 0 | 100 | 0 |
| | 5 | 100 | 0 |
| | 35 | 76 | 24 |
| | 37 | 0 | 100 |
| | 42 | 0 | 100 |
| | 45 | 100 | 0 |
| | 50 | 100 | 0 |

The collected fractions are neutralized with acetic acid (pH=7) and then salts are removed by incubating for five minutes with an anion exchanger (TMD8 mixed bed resin, from Sigma, article number M8157) in a batch process while shaking at room temperature. The ion exchanger is removed from the solution by centrifugation and filtration through a 0.2 µm filter (ultrafree-MC, from amicon, article number UFC3 0LG 25).

The fractions are frozen and concentrated to dryness in the frozen state in a vacuum concentrator. The corresponding fractions from the four runs are combined in a total of 250 µl of deionized water.

To determine the proportion of the various oligomers, the individual fractions are hydrolyzed with exo-inulinase to glucose and fructose. The fractions are diluted where appropriate. 100 µl of fraction solution are digested with 0.25 U of exo-inulinase (from Megazyme, article number E-EXO1) at 37° C. for three hours. The reaction is stopped by incubating at 95° C. for 10 minutes. After cooling, the solution is filtered (ultrafree-MC, from amicon, article number UFC3 0LG 25). 150 µl of the filtrate are fractionated by ion exchange chromatography with gradient 2 and the following wave form of the detector:

| Time (s) | Potential (V) | |
|---|---|---|
| 0.00 | 0.05 | |
| 0.20 | 0.05 | Start of integration |
| 0.40 | 0.05 | End of integration |
| 0.41 | 0.75 | |
| 0.60 | 0.75 | |
| 0.61 | −0.15 | |
| 1.00 | −0.15 | |

The HPAEC-PAD system is calibrated with glucose and standard fructose solutions in the 6 µM-30 µM concentration range. The concentrations of the glucose and fructose liberated in the fractions are determined with the aid of this calibration (in µmol/l).

To calculate the percentage content of the oligomers from DP3 to DP10 in the total inulin, the total of the glucose and fructose liberated for the respective oligomer is divided by the weight of the purified artichoke inulin (2% strength solution).

7. Determination of the Water Content

The water content is determined using an AQUA 40.00 Karl-Fischer titrator (from analytikjena AG). Hydranal-Coulomat AG (Riedel-deHaën, article No. 34836) is used as anolyte. The reference substance used is dibasic sodium tartrate dihydrate (Riedel-deHaën, article No. 32323) with a moisture content of 15.61-15.71%. 10-20 mg of sample are weighed into 5 ml sample bottles (N20-5DIN, Machery-Nagel, article No. 702 04.36), the bottles are closed with crimped caps (N20 TS/oA, Machery-Nagel, article No. 702 815), and the water content of the sample is determined using the Karl-Fischer titrator.

8. Preparation of Inulin Pastes 10.5 g of inulin (dry substance) are dispersed in 59.5 ml (of water or citrate buffer of pH 4.0) in a 150 ml glass beaker using a small whisk (3-loop; 2 cm wide; 8.6 cm long) which is driven by an IKA RW16 basic stirrer (IKA Werke GmbH und Co. KG, 79219 Staufen, Germany) at setting 6-7, by continuous addition of the inulin over a period of 30 s. The dispersion is then transferred into a 250 ml measuring cylinder (diameter 35 mm; height 160 mm) and sheared using an Ultra-Turrax T25 (T25 basic disperser) (IKA Werke GmbH und Co. KG, 79219 Staufen, Germany) at 24 krpm for 3 minutes. The contents of the vessel are not cooled. The inulin pastes are then transferred into a 100 ml glass beaker, covered with a glass lid and stored in a refrigerator at 13° C. overnight. Before each subsequent measurement, the inulin pastes are conditioned at room temperature for one hour. They are then stirred until smooth with a long paddle stirrer (2 stirrer paddles on a 1 cm-thick axle; width of paddle 1.4 cm; length of paddle 5.9 cm) which is driven by an IKA RW16 basic stirrer (IKA Werke GmbH und Co. KG, 79219 Staufen, Germany) at 100 rpm for 5 minutes. Immediately thereafter, the pastes are transferred into the respective measuring vessels.

9. Determination of the Shear Stability of Inulin Pastes

The shear stability of aqueous inulin pastes is measured using a Rotovisko VT550 viscotester (from: formerly Thermo Haake GmbH, now Thermo Electron GmbH, 63303 Dreieich, Germany) at a measurement temperature of 20-22° C. using an inclined paddle stirrer at 128 rpm in a measuring cup (diameter 42 mm; height 93 mm). For this purpose, the inulin pastes were stirred in the Rotovisko for 15 minutes and the viscosity of the pastes was measured in each case at the start (highest point of the curve) and end of the stirring period. The relation of the viscosity at the end of the stirring process ($Visc_2$) to the viscosity at the start ($Visc_1$) is then calculated, and the shear stability is thus determined:

$$\text{Shear stability [\%]} = Visc_2/Visc_1 * 100$$

10. Determination of the Acid Stability of Inulin Pastes

Inulin pastes in citrate buffer of pH 4 are prepared to determine the acid stability. Determination of the stability in an acidic medium takes place in analogy to the determination of the shear stability, i.e. using a Rotovisko VT550 viscotester at a measuring temperature of 20-22° C. using an inclined paddle stirrer at 128 rpm in a measuring cup (diameter 42 mm; height 93 mm). The inulin pastes are stirred in the Rotovisko for 15 minutes and the viscosity of the pastes is measured in each case at the start and at the end of the stirring period. The relation of the viscosity at the end of the stirring period ($Visc_2$) to the viscosity at the start ($Visc_1$) is then calculated, and the acid stability is thus determined:

$$\text{Acid stability [\%]} = Visc_2/Visc_1 * 100$$

11. Determination of the Thermal Stability of Inulin Pastes

The thermal stability of inulin pastes is determined in a DSR rheometer (formerly Bohlin Instruments GmbH, 75181 Pforzheim, Germany; since 10/2004: Malvern Instruments GmbH, 71083 Herrenberg, Germany) with the following configuration:

| | |
|---|---|
| Measuring system: | cone (4°)/plate |
| Rate: | 0.1 Hz |
| Strain: | 0.001 |
| Initial Stress: | 0.6 Pa |
| Temperature profile: | 30° C.-90° C. (1° C./minutes) |

The temperature defined as the melting temperature of the inulin pastes is that at which the viscosity of the gels is less than 2 Pas.

12. Differential Scanning Calorimetry of Inulin 3 g portions of inulin (dry substance) are weighed into 50 ml graduated polypropylene tubes (30.0×115 mm, from Greiner, order number 227261). 18 ml of double-distilled water are added to the respective powder and shaken. All the available suspensions are then placed in a water bath (95° C.) and dissolved by shaking several times. It is established visually after 20 minutes that all the suspensions have completely dissolved. The available solutions are then made up to 20 ml by means of the graduation of the polypropylene tube to afford a 15% strength solution (w/v).

The solutions are then immediately put, while still hot, completely into Petri dishes (100×20 mm, from Greiner, order number 664102) and dried with the lid open at 37° C. for 2 days. After this time, the available dried material is transferred into a mortar and ground for 2-3 minutes. This powder is then homogenized in a hammer mill (MM 300 from Retsch) with an adapter which comprises a steel ball with a diameter of 20 mm for 30 s and at a frequency of 30 Hertz. The powder is then transferred into a closeable vessel and employed for DSC measurements.

The water content of the samples is determined by means of an automatic Karl-Fischer titrator (see general methods 7.)

For a DSC measurement, about 10 mg of inulin dry substance are weighed into a stainless steel pan (volume 50 µl), the exact weight is determined, and 30 µl of distilled water are added. The pans are then hermetically sealed. An empty stainless steel pan is used as reference. The sample is heated in a DSC apparatus with autosampler (Perkin Elmer; Diamond) from 10-160° C. at a heating rate of 10° C./minutes. The data analysis is carried out by a PYRIS 7.0 software program (Perkin Elmer, 63110 Rodgau-Jügesheim, Germany). In this case To (onset) and the free enthalpy dH were determined.

13. Determination of Viscosity

Inulin solutions at 90° C. temperature: Viscosity versus concentration:

An aqueous suspension of inulin was produced by filling up the inulin amount with the respective volume of distilled water (weight per volume). The resulting suspension was heated and dissolved in a water bath to 95° C. under constant stirring.

The measurements were executed on a CVO 120HR Bohlin/Malvern rheometer applying the isothermal (90° C.) viscometry mode on a cone-plate-system CP4°/40 mm. As pre-shear a shear rate of 10/sec. was applied for 60 sec. with 10 sec. relaxation time. The shear was measured in shear rate mode with logarithmic sweep type steps. Starting shear rate was 20/sec., end shear rate 30/sec. in an ascending ramp with 20 sec. hold up time and 10 sec. integration time. The data was taken at a shear rate of 20 $s^{-1}$.

14. Determination of Gel Strength and Viscoelastic Behaviour 70 g of a 10-25 wt.-% suspension of inulin in water (distilled) were filled in a measuring cup MV of a Haake Rotovisco VT 550 viscosimeter. Subsequently, a blade agitator was inserted and installed in the preheated (90° C., temperature jacket) device. Then, the preparation was heated for 15 min under stirring at 128 rpm.

After 15 min the preparation at 90° C. was transferred into a container consisting of a bottom and a wall of two cylindrical rings from acrylic glass (each 20 mm height, 30 mm diameter) lying upon each other and fitted to each other by an adhesive tape (19 mm width). The preparation was filled into the container up to a level of about 5 mm below from the upper edge without bubbles. Then, the container was hermetically sealed with an aluminium foil and left at room temperature (23° C.) over night.

The measurement of gel strength was done after storing for about 20 hours at room temperature (23° C.) with a Texture Analyser TA XT2. In order to allow a measurement of gel strength at a smooth, undried surface, at first the adhesive tape holding the two cylindrical rings of the container together was removed. Subsequently the gel was cut through between the rings with a knife blade so that the lower part of the gel showed a smooth surface.

Measurement of gel strength with the Texture Analyser TA XT2 was done by penetration (depth 1 mm) of a plane swivel (24.5 mm diameter) into the gel. Settings at the Texture Analyser were as follows:

| measuring principle: | force in direction of pressure |
| pre-velocity: | 2 mm/s |

| test velocity: | 2 mm/s |
| trigger value | 0.01 N |
| return velocity | 2 mm/s |
| distance | 1 mm |

The maximum value for a one time penetration of the calotte is given in Newton.

Viscoelastic Behavior after Cool Down to 25° C.

Aqueous inulin solutions of different concentrations were prepared as already described in the determination of viscosity (see above) and cooled down subsequently. The cooling rate was constantly maintained at 1K per min. via automatic temperature control. After reaching 25° C. the frequency sweep was instantly applied. The measurements were executed on a CVO 120HR Bohlin/Malvern rheometer applying the isothermal (25° C.) oscillation mode on a cone-plate-system CP4°/40 mm. No pre-shear was applied. Stress was measured in logarithmic sweep type steps with 10 sec. hold up time. Starting frequency was 0.100 Hz, end frequency 5.000 Hz0/sec. in an ascending ramp. Stress was adjusted to γ=0.010 (supposed deformation) automatically starting at σ=0.100 Pa.

15. Fermentation Study

Faecal Samples 10 contributors for faecal samples were selected in consideration of the following exclusion criteria:
- no treatment with antibiotics during the last 6 months
- no permanent treatment with medicaments of any kind, except oral contraceptives
- no indisposition during the week preceding the contribution
- no symptoms of diarrhoea during the week preceding the contribution
- no nutrition by a special therapeutical diet
- no special selection of food for purpose of weight reduction Faecal Samples for the experiment were taken not earlier than 1 hour before beginning of the experiment. About 4 g faecal sample were weighted out exactly and diluted 1:10 with Wilins-Chalgren anaerobical (WCA)-medium aerated with $N_2/CO_2$ (80/20, v/v). For homogenisation, samples were filled into a Stomacher™ Lab Blender bag and treated at maximum speed in a Stomacher™ Lab Blender. The necessary period was between one and ten minutes depending of the sample consistency.

1 ml of the diluted and homogenized faecal samples, respectively, was inoculated under aseptic conditions into Hungate culture tubes and mixed with medium that was previously filled in. The tubes contained 9 ml WCA-medium aerated with $N_2/CO_2$ (80/20, v/v), wherein in the WCA medium the evaluated carbohydrates were in such concentrations that a final concentration of 10 mM, calculated in relation to the monomer, was obtained after addition of the diluted faecal sample. The cultures prepared in such a way were incubated for 24 h at 37° C. Samples of 4 ml, respectively, were taken prior to the beginning of incubation and after 24 h for subsequent analysis.

Pretreatment of Samples

The samples taken from the Hungate tube were split up to two 2 ml reaction vessels, respectively, and centrifuged for 10 min at 8000×g. The supernatants were decanted and frozen at −20° C. up to the evaluation of parameters. The sedimented cells were resuspended in 1.5 ml 1×PBS by intense mixing together with three 3 mm glass beads and centrifuged at 300×g for 1 min in order to remove coarse particles. Subsequently, 1 ml of the supernatant was mixed with 3 ml of paraformaldehyde solution and incubated for 3 h at 4° C. Then, 1 ml of the suspension was centrifuged at 8000×g for 3 min and the pellet was mixed with 300 µl 1×PBS and stored at −20° C. after addition of 300 µl ethanol (absolute).

Determination of the Cell Titer

The analysis for determination of cell titer by FISH microscopy was done according to the procedure of Thiel & Blaut (Thiel, R., Blaut, M. (2005) Microbiol. Meth. 61, 369-379).

Probes for Determination of Cell Number

Cells present in the samples were analysed by the method of automatical FISH microscopy. For determination of total number of cells the probe mixture EUB-mix (EUB 338: Amann et al., 1990, Appl. Environ. Microbiol. 56, 1919-1925; EUB 785, EUB 1055 und EUB 1088: Lee et al., 1993, Mar. Ecol. Prog. Ser. 101, 193-201; EUB 927: Giovannoni et al., 1988, J. Bacteriol. 170, 720-726) was used. The determination of Lactobacilli was done with probe Lab158 (Harmsen et al., 1999 Microb. Ecol. Health Dis. 11:3-12) by manual counting due to the low cell titers expected.

Detection of $H_2$-Production

The detection of hydrogen was done with a HP 6890 series II gaschromatograph having a HP-19091P-MS4 molecular sieve-5A capillary column (30 m×0.32 mm×12 µm film thickness) with a heat conductivity detector. As carrier gas $N_2$ with a flow of 1 ml/min was used. The temperature of column furnace was 40° C., the temperature of the detector was 205° C. The split was adjusted to 1:10 and the injection volume was 0.5 ml.

Determination of Fructose

The fructose content of samples was determined with the Fructan Assay Kit (Megazyme Cat No: K-FRUC) under adjustment to the provided sample volumina. The fructose content is a measure for residual inulin in the fermentation samples since inulin is converted to fructose.

16. Food Preparations a) Low Fat Salad Dressing

| Ingredients[1] | Recipes / Type of inulin used | | | | |
|---|---|---|---|---|---|
| | Artichoke, mean DPw 56 Weight (g) | — (control) Weight (g) | Cargill Oliggo-Fiber LC/HT Weight (g) | Cargill Oliggo-Fiber F97 Weight (g) | Orafti Raftiline HP Weight (g) |
| Oil Phase: | | | | | |
| Soybean Oil | 92.45 | 302.45 | 92.45 | 92.45 | 92.45 |
| Eggs, whole, pasteurized | 23.00 | 23.00 | 23.00 | 23.00 | 23.00 |
| Egg Yolks, pasteurized | 18.00 | 18.00 | 18.00 | 18.00 | 18.00 |
| Aqueous Phase: | | | | | |
| Buttermilk, cultured, lowfat | 89.45 | 89.45 | 89.45 | 89.45 | 89.45 |
| Water | 190.45 | 40.45 | 190.45 | 190.45 | 190.45 |
| Vinegar, white distilled | 8.00 | 8.00 | 8.00 | 8.00 | 8.00 |
| Parsley, whole flakes, dehydrated | 0.50 | 0.50 | 0.50 | 0.50 | 0.50 |
| Potassium Sorbate | 0.10 | 0.10 | 0.10 | 0.10 | 0.10 |
| Dry Blend A | | | | | |
| Salt | 3.75 | 3.75 | 3.75 | 3.75 | 3.75 |
| Mustard Flour | 1.50 | 1.50 | 1.50 | 1.50 | 1.50 |
| Dry Blend B | | | | | |
| Inulin | 60.00 | — | 60.00 | 60.00 | 60.00 |
| Sugar, granulated | 8.00 | 8.00 | 8.00 | 8.00 | 8.00 |
| Salt | 2.25 | 2.25 | 2.25 | 2.25 | 2.25 |
| Black Pepper, medium | 1.00 | 1.00 | 1.00 | 1.00 | 1.00 |
| Garlic Powder | 1.00 | 1.00 | 1.00 | 1.00 | 1.00 |
| Onion Powder | 0.50 | 0.50 | 0.50 | 0.50 | 0.50 |
| Xanthan Gum | 0.05 | 0.05 | 0.05 | 0.05 | 0.05 |

[1]Suppliers (all supplier names and product names are registered trademarks):
Soybean Oil from AC Humko.
Whole eggs and egg yolks (10% salt) from Sysco
Vinegar from Fleischmann's (20% acidity)
Whole parley flakes and Black pepper from McCormick
Potassium Sorbate from ADM
Salt from Morton
Mustard flour from French's (82841)
Granulated sugar from C&H
Garlic powder and onion powder from ConAgra/Gilroy
Xanthan gum from Kelco (Keltrol 521)

Preparation:
1. Dissolve potassium sorbate in water.
2. Add blend B under shear.
3. Add vinegar followed by buttermilk under shear.
4. Add egg yolks and whole egg.
5. Add dry blend A under shear.
6. Slowly add oil blend under shear.
7. Fold in parsley flakes while mixing at low speed or by hand.
8. Keep refrigerated.

b) White Bread

| | Recipes | | | | |
|---|---|---|---|---|---|
| | Type of inulin used | | | | |
| Component[1] | Artichoke, mean DPw 56 Weight (g) | — (control) Weight (g) | Cargill Oliggo-Fiber LC/HT Weight (g) | Cargill Oliggo-Fiber F97 Weight (g) | Orafti Raftiline HP Weight (g) |
| Bread Flour, 12.6% protein | 357.20 | 391.80 | 357.20 | 357.20 | 357.20 |
| Water | 300.30 | 300.30 | 300.30 | 300.30 | 300.30 |
| Pastry Flour, 9.5% protein | 135.80 | 148.90 | 135.80 | 135.80 | 135.80 |
| Shortening, hydrogenated | 48.40 | 48.40 | 48.40 | 48.40 | 48.40 |
| Sugar, granulated | 48.40 | 48.40 | 48.40 | 48.40 | 48.40 |
| Inulin | 47.70 | — | 47.70 | 47.70 | 47.70 |
| Invert Sugar | 29.80 | 29.80 | 29.80 | 29.80 | 29.80 |
| Non fat dry milk, Nth Inst Bulk | 14.90 | 14.90 | 14.90 | 14.90 | 14.90 |
| Yeast, instant | 8.60 | 8.60 | 8.60 | 8.60 | 8.60 |
| Salt | 6.00 | 6.00 | 6.00 | 6.00 | 6.00 |
| Distilled Monoglyceride | 1.70 | 1.70 | 1.70 | 1.70 | 1.70 |
| Emulsifier | 1.10 | 1.10 | 1.10 | 1.10 | 1.10 |
| Bakery Enzyme | 0.10 | 0.10 | 0.10 | 0.10 | 0.10 |

1)Suppliers (all supplier names and product names are registered trademarks):
Bread flour and pastry flour from General Mills (Superlative #53521; Superlative #58431)
Shortening from Loders Croaklaar (321)
Granulated sugar from C&H
Invert sugar from LSI (Nulomoline)
Non fat dry milk from Kerry (I1532)
Instant yeast from Fleischmann's (2139)
Salt (Table) from Morton
Distilled Monoglyceride (Domodan PH 300 K-A), Emulsifier (Panodan Datem 205K) and Bakery Enzyme (Grindamyl Max-Life U4) from Danisco Preparation:
1. Weigh together dries except salt in KitchenAid bowl.
2. Add invert sugar, shortening and water and mix for 1 minute at "stir" speed.
3. Add salt and continue to mix for 1 minute at "stir" speed and 6 minutes at "1" speed.
4. Proof for 1½ hours at 29° C. in a covered bowl.
5. Punch down dough and shape into loaf and put into greased loaf pan.
6. Allow to proof until doubled about 1½ hours.
7. Bake at 200° C. convection oven for 30 min. until lightly golden and internal temperature is 96° C.-100° C.
8. Rotate pan once during baking.
9. Cool on rack for 5 minutes, remove loaf pan and cool to room temperature.

Example 1

Characterization of the Inulin from Artichoke Roots

1. Cultivation of the Artichoke Plants

Artichoke plants of the Nun9444 (also referred to as N9444) variety were grown in the vicinity of Valencia, Spain. The seeds were sown in June in plant boxes with 104 recesses (8×13 holes, 4×4 cm) in a mesh plant house. The plants were cultivated in the plant boxes for six weeks. The plants were planted out in a field at a density of 10 000 plants/ha at the start of August. The whole plants were harvested in July of the following year. The roots were separated from the part above ground and freed of adherent soil with water (under pressure) and additionally by hand. The roots were dried on a fixed substrate in the shade for 3 days. The roots were then transported without chilling from Spain to Germany. The roots were stored at −80° C. until the inulin was extracted.

2. Inulin Preparation from Artichoke Roots

For the inulin preparation, artichoke roots of the Madrigal (formerly Nun 9444) variety were thawed at room temperature and cut into pieces. The inulin was extracted and purified as described in the "Inulin purification and fractionation" method described above. The purified inulin from a plurality of preparations was combined to give a sample.

3. Determination of the Purity of the Prepared Inulin

The purity of the prepared artichoke inulin was determined by determining the fructan and water contents of the freeze-dried material. A water content of 5.4% was determined for the artichoke inulin (see "Determination of the water content" method).

To determine the fructan/inulin content, 20 mg of artichoke inulin were incubated in 2 ml of double-distilled water with shaking in a heating block at 95° C. for one hour. The fructan/inulin content was determined both (1) with the "Fructan Assay Procedure" kit (see method 2.1) and (2) by hydrolyzing the inulin using exo-inulinase and subsequent enzymatic determination of the content of liberated glucose and fructose (see method 2.2). The samples were diluted 1:5 with double-distilled water for (1). The purity based on dry matter (DM) was determined from the fructan content and the water content. Purity=fructan content×100/(100−water content)

As is evident from table 1, the average degree of purity of the prepared artichoke inulin is 92.5 or 99.1% of dry matter (DM), depending on the determination method.

TABLE 1

Determination of the purity of the prepared artichoke inulin

| Material | Water content [%] | (1) Fructan Assay Procedure | | (2) Exo-inulinase digestion | |
|---|---|---|---|---|---|
| | | Fructan [% of initial weight] | Purity [% DM] | Fructan [% of initial weight] | Purity [% DM] |
| Artichoke inulin | 5.4 | 86.5 ± 2.2 | 91.5 ± 2.2 | 94.5 ± 4.1 | 99.1 ± 4.1 |

Figure 1:
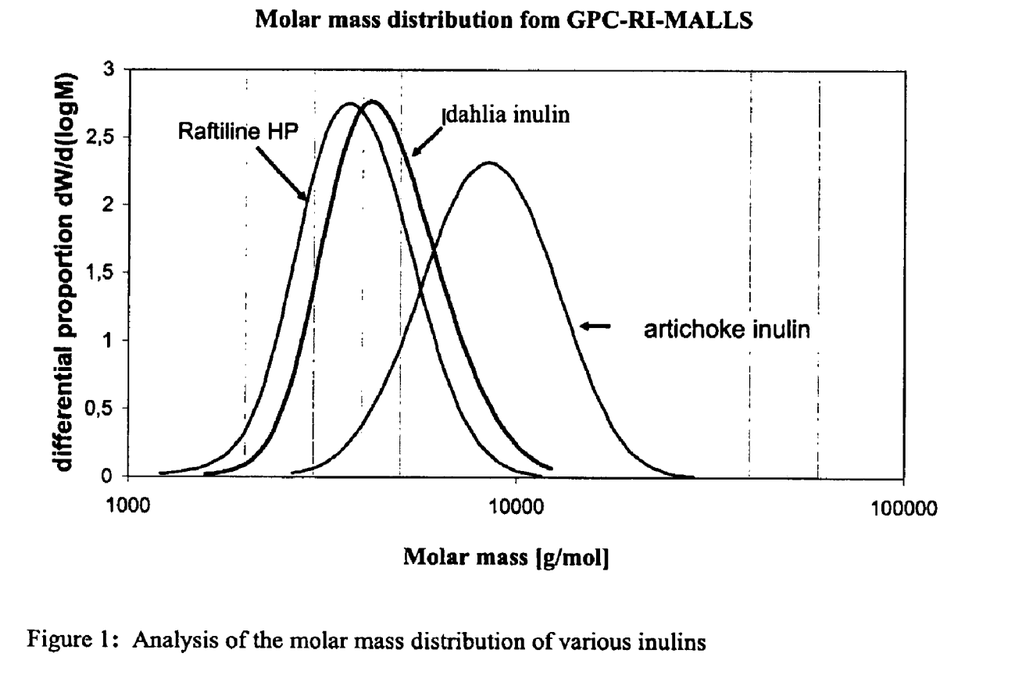
Figure 1: Analysis of the molar mass distribution of various inulins

4. Molecular Weight Determination by GPC-RI-MALLS 0.5% (w/v) aqueous solutions were prepared from purified artichoke inulin and from purchased reference samples of Raftiline HP (from Orafti, batch: HPBNO3DNO3) and inulin from dahlia tubers (from Sigma, article number I-3754, batch: 022K7045 or 75H7065) and the molar mass distribution of the inulins was determined by gel permeation chromatography (see method 4). This distribution is depicted in FIG. 1, and the molar masses (anhydrofructose=162 g/mol) and average chain lengths calculated therefrom have been compiled in table 2.

Analysis of the molecular weight distribution using the GPC-RI-MALLS system resulted in a weight-average molar mass $M_w$ of 9045 g/mol and a number-average molar mass $M_n$ of 7797 g/mol for the artichoke inulin. This corresponds to an average chain length of 56 for DPw and 48 for DPn. The chain lengths of the purified artichoke inulin are on average distinctly longer than those of Raftiline HP (DPw=25, DPn=23) and of dahlia inulin (DPw=29, DPn=26). This is also reflected in the minimum and maximum molar masses, which are distinctly larger for the artichoke inulin.

TABLE 2

Molar mass distribution of various inulins

| Material | $M_w$ [g/mol] | $M_n$ [g/mol] | Polymer distribution (min-max) [g/mol] | DPw | DPn | Molecular dispersity |
|---|---|---|---|---|---|---|
| Artichoke inulin | 9045 ± 45 | 7797 ± 46 | 2650-28 630 | 56 | 48 | 1.17 |
| Raftiline HP | 4120 ± 28 | 3673 ± 45 | 1210-11 610 | 25 | 23 | 1.09 |
| Dahlia inulin | 4734 ± 68 | 4242 ± 50 | 1590-12 300 | 29 | 26 | 1.11 |

4a Determination of Molecular Weight with Perchloro Acetic Acid (PCA) Hydrolysis

TABLE 2a

| DPn | 1. measurement | 2. measurement |
|---|---|---|
| Inulin from artichoke | 51 | 48 |
| Raftiline HP | 27 | — |
| Inulin from dahlia | — | 35 |

1. measurement: 4.5% inulin end concentration, 0.5% TCA end concentration, 24 h, 56° C.
2. measurement: 2.5% inulin end concentration, 9% TCA end concentration, 4 h, 37° C.

5. Results of Glucose, Fructose and Sucrose Determination

To determine the proportion of glucose, fructose and sucrose in the purified artichoke inulin, 1% and 2% strength aqueous inulin solutions were prepared and incubated at 95° C. for one hour. This was followed by photometric determination of the sugars as described in method 3 ("sugar determination").

As is evident from table 3, fructose is detectable in the purified artichoke inulin only with a content of 0.1%. Glucose and sucrose were not detectable under the described conditions with the photometric detection method.

TABLE 3

Content of glucose, fructose and sucrose in purified artichoke inulin

| Material | Glucose (g/100 g of inulin powder) | Fructose (g/100 g of inulin powder) | Sucrose (g/100 g of inulin powder) |
|---|---|---|---|
| Artichoke inulin | Not detectable | 0.1 | Not detectable |

6. Determination of the Percentage Content of Oligofructans with a Chain Length of from DP=3 to DP=10 in the Total Inulin by HPAEC-PAD To calculate the percentage content of oligofructans with a chain length of from DP=3 to DP=10 in the total inulin, 2% (w/v) aqueous solutions of the purified artichoke inulin were prepared and fractionated by HPAEC-PAD (method 5), and the proportions of the oligofructans were calculated by method 6. The values resulting from this were as follows

| Inulin oligomer | Content (g/100 g of powder) |
|---|---|
| DP3 | 0.007 |
| DP4 | 0.016 |
| DP5 | 0.012 |
| DP6 | 0.013 |
| DP7 | 0.024 |
| DP8 | 0.029 |
| DP9 | 0.044 |
| DP10 | 0.072 |
| Total | 0.217 |

Example 2

Characterization of Inulin Pastes

1. Determination of the Stability of Inulin Pastes

Analysis of the stability of inulin pastes (procedure: see methods) showed that the stability behavior of the artichoke inulin is distinctly altered compared with that from chicory (Raftiline HP) and that from dahlia (see table 4). At the shear rates used herein, the artichoke inulin showed the greatest stability with more than 90% of the initial value. Analysis of the viscosity stability of the inulin pastes in an acidic medium (acid stability) additionally showed that the artichoke inulin displays the smallest change after storage for 2 weeks from the initial value after 24 h, and the viscosity rose by only 6.7%. In contrast thereto, the viscosity of the dahlia inulin paste increased in an acidic medium by more than 15% and that of Raftiline HP by more than 32%. This after-thickening is undesired in many applications in the food sector. The melting temperature of the artichoke inulin pastes was 73° C. which is distinctly higher than that of the comparison substances, i.e. 62.3° C. for Raftline HP (from Orafti, batch: HPBNO3DNO3) and 65.5° C. for dahlia inulin (from Sigma, article number 1-3754, batch: 75H7065). A high thermal stability of inulin pastes is a very great advantage in many thermal processes in the food sector.

TABLE 4

| Material | Shear stability [%] | Acid stability [%] | Melting temperature [° C.] |
|---|---|---|---|
| Artichoke inulin | 90.5 | 106.7 | 73.0 |
| Raftiline HP | 49.8 | 132.1 | 62.3 |
| Dahlia inulin | 81.0 | 115.9 | 65.5 |

2. Differential Scanning Calorimetric Investigation of Inulin

Figure 2:
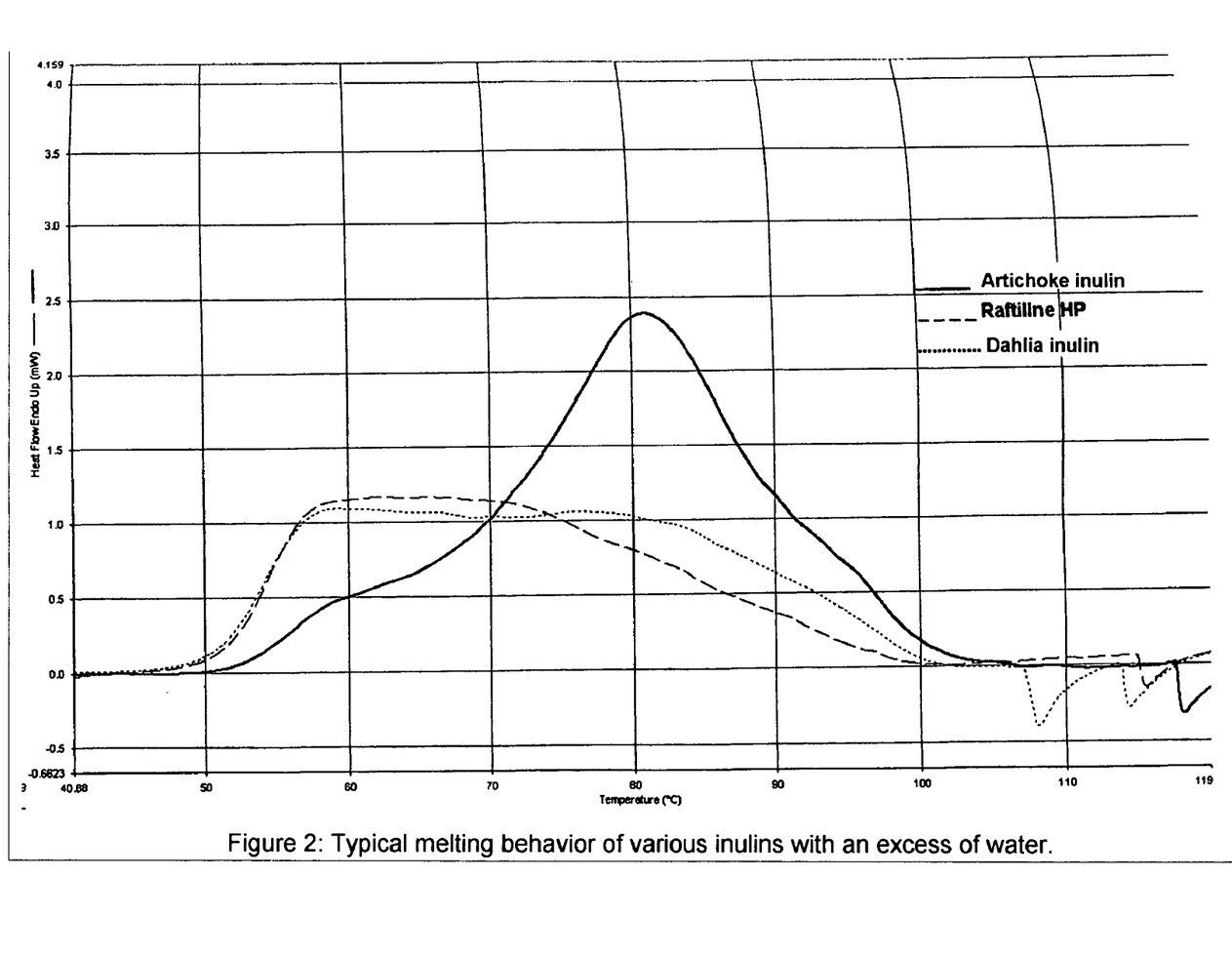
Figure 2: Typical melting behavior of various inulins with an excess of water.

The differential scanning calorimetric analysis of inulin (procedure: see methods) showed clear differences between the various materials (see table 5) in relation to the melting behavior. Although $T_{onset}$ (To) was very similar for all inulin samples, they differed greatly in the enthalpy of fusion. This was more than 30 J/g for artichoke inulin, only 21.3 J/g for Raftiline HP and 22.9 J/g for dahlia inulin. In addition, the shape of the melting curve of artichoke inulin was distinctly different from that for the two other inulins (see FIG. 2). The melting curve of the artichoke inulin initially has a much shallower course than that of the two other inulins, but then rises much further than with Raftiline HP or dahlia inulin (FIG. 2). This increased thermal stability of artichoke inulin may be a considerable advantage in certain thermal processes in the food sector, because artichoke inulin is distinctly less sensitive to high temperatures than Raftiline HP or dahlia inulin.

TABLE 5

| Material | To [° C.] | Enthalpy of fusion dH [J/g] |
|---|---|---|
| Artichoke inulin | 51.6 | 30.2 |
| Raftiline HP | 51.2 | 21.3 |
| Dahlia inulin | 51.1 | 22.9 |

Example 3

Viscosity, Gelling Behaviour, Solubility a) Viscosity

TABLE 6

Comparison of the dynamic viscosity of chicory and artichoke inulin in water as a function of concentration (T = 90° C.)

| | Viscosity (mPas) | |
|---|---|---|
| Concentration (w/v) | Raftiline ® HP (chicoree) mean DPw 25 | Inulin from Artichoke, mean DPw = 56 |
| 20 | 2.2 | 3.0 |
| 22.5 | 2.4 | 3.4 |
| 25 | 3.1 | 8 |
| 30 | 2.7 | 550 |

As can be seen from the above table, at concentrations up to 22.5% both inulins displayed very low viscosities at 90° C. (water=1 mPas). When concentrations were 25% (w/v) inulin of the invention started to become viscous while Raftiline HP remained very similar to water up to 30% (w/v). At 30%, inulin of the invention showed an unexpectedly high viscosity.

b) Gelling Behaviour

The gelling behaviour of inulins after thermal solubilisation was done by two types of analysis.

Inulins were those described in Table 2 and Example 2. First different concentrations of inulins from artichoke (of the invention), Raftiline HP and inulin from dahlia were heated to 90° C. and subsequently cooled for 20 h at room temperature. The gels that were formed displayed a particle type character ("particle gels"). Gel strength was quantified by texture analysis and the values are given in the table below. At a given concentration of 20% (w/v), the gel made from artichoke inulin was very strong, no gel formation was observed for Raftiline HP and only a pudding-like consistency was obtained with inulin from Dahlia.

TABLE 7

Strength of gels from thermally dissolved inulin

| | Gel strength [N] | | |
|---|---|---|---|
| Concentration (w/v) | Raftiline HP | Artichoke | Dahlia |
| 10% | No gel | No gel | No gel |
| 15% | No gel | No gel | 3.2 |
| 20% | No gel | >50 | 4.4 |
| 25% | 12.6 | >50 | >50 |

A more detailed characterisation of gel formation and stability was performed with a dynamic rheometer. Different concentrations (w/v) of Raftiline HP and Inulin from Artichoke of the invention (mean DPw 56) were solubilised in water at 90° C. and subsequently cooled at 1° C./min to 25° C.

TABLE 8

| | Elastic modulus G' at 5 Hz [Pa] | | Viscous modulus G" at 5 Hz [Pa] | |
| --- | --- | --- | --- | --- |
| Concentration (w/v) | Raftiline ® HP (chicoree) mean DPw = 25 | Inulin from Artichoke, mean DPw = 56 | Raftiline ® HP (chicoree) mean DPw = 25 | Inulin from Artichoke, mean DPw = 56 |
| 15 | not detectable | 2.5 | not detectable | 1.9 |
| 20 | 13.0 | 171.3 | 12.4 | 134.4 |
| 22.5 | 12.8 | 636900 | 14.2 | 20880 |

The results in the above table indicate that at 20% to 22.5% Raftiline HP did not display gelling behaviour (G">G'; viscous modulus>elastic modulus). In contrast to that, artichoke inulin of the invention formed already very solid gels at the same concentrations.

c) Solubility

In another experiment a 20% (w/v) solution of Raftiline, inulin from dahlia and inulin from artichoke prepared at 98° C. and subsequently been stored in a refrigerator. Afterwards the amount of inulin still being in solution was quantified. Inulins were those as described in Table 2 and Example 2.

TABLE 9

| | Solubility of different inulins | | |
| --- | --- | --- | --- |
| | Chicory | Artichoke | Dahlia |
| Solubility [%] | 97.2 | 14.2 | 88 |

As shown in the table above, Raftiline was by far the best soluble, closely followed by inulin from dahlia, whereas inulin from artichoke was only soluble to a minor extent.

These observations imply that at intermediate (below 60° C.) or low temperatures higher amounts of artichoke inulin can be introduced into foodstuff (such as drinks, dressings etc.) without affecting the viscosity than with other commercially available inulins. This is a great benefit in food applications.

Example 4

Fermentation Study a) Fermentation Rates

Artichoke inulins of DP 58 (batches A und B) and Raftilin HP were fermented by human faecal bacteria as indicated by a production of $H_2$ gas achieved compared to a control without inulin.

The following table shows the inulin contents (residual inulin+standard deviation) in the fermentation preparations after 24 h in percent of the originally employed quantity of inulin (average values of independent fermentation preparations for each of the substrates, n=10).

TABLE 10

| sample | residual-inulin (%) | p-values* |
| --- | --- | --- |
| Raftiline HP | 2.6 +/− 1 | |
| Artichoke inulin batch A | 9.0 +/− 3 | 0.00002 |
| Artichoke inulin batch B | 10.0 +/− 4 | 0.00010 |

*significance of deviation in comparison to Raftiline HP (T-test for paired spot samples)

The table shows that after 24 h of fermentation more residual inulin was present in the inventive sample (artichoke inulin, mean DPw 58) than in the sample with Raftiline HP. Thus artichoke inulin with a DP of 58 is fermented by faecal bacteria more slowly than the commercial Raftilin HP. A slower fermented very long chain inulin, as the inventive inulin, would be expected to exert the metabolic and prebiotic effects in more distal parts of the colon, as compared to commercial inulins. Fermentation in the distal colon is beneficial, since many intestinal diseases (e.g. ulcerative colitis, divertical disease) are mainly located here.

b) Prebiotic Effects

The following table shows the increase of Lactobacilli (Lab) number after 24 h caused by fermentation, corrected against a blank sample (without inulin) in percent, and the number ratio of Lactobacilli to Eubacteria (Eub) after 24 h of fermentation (average values of independent fermentation preparations for each of the substrates, n=10).

TABLE 11

| sample | increase of Lactobacilli (%) | Lab/Eub |
| --- | --- | --- |
| Raftiline HP | 81 | 0.62 |
| Artichoke inulin batch A | 119 | 0.87 |
| Artichoke inulin batch B | 100 | 0.81 |

Artichoke inulin of the invention stimulated the numbers of Lactobacilli to higher levels than Raftiline HP. The superior effect of artichoke inulin versus Raftiline HP in respect to stimulation of Lactobacilli, becomes even more consistent if the ratio of Lactobacilli/Eubacteria is considered, which is significantly higher with inulin of the invention. This value is even more appropriate to express the specific stimulatory effect on desired Lactobacilli.

Example 5

Food Applications a) Low Fat Salad Dressing

TABLE 12

| | Inulin (Source) | | | | |
| --- | --- | --- | --- | --- | --- |
| | Inulin according to invention from Artichoke | — (control) | Cargill Oliggo-Fiber ™ LC/HT (Chicory) | Cargill Oliggo-Fiber ™ F-97 (Chicory) | Orafti Raftiline ® HP (Chicory) |
| mean DPw | 56 | | >20 | 70% is <10 | 25 |
| Mono & Disaccharides | <0.5% | | 1.0% | 3.0% | |
| Moisture Content | 5.40% | | 4.00% | 5.00% | 3.00% |

TABLE 12-continued

| | Inulin (Source) | | | | |
|---|---|---|---|---|---|
| | Inulin according to invention from Artichoke | — (control) | Cargill Oliggo-Fiber™ LC/HT (Chicory) | Cargill Oliggo-Fiber™ F-97 (Chicory) | Orafti Raftiline ® HP (Chicory) |
| Organoleptic Attributes: | | | | | |
| Appearance | Slightly thicker vs control; similar cling | Typical Ranch; creamy, off-white color; stays on salad | Slightly thinner vs control; similar cling | Much thinner than control; does not cling to salad | Thicker than control; does not pour |
| Aroma | Similar to control | Typical | Similar to control | Similar to control | Similar to control |
| Texture | n/a* | Full fat, creamy mouthfeel | Thin mouthfeel, lacking fat fullness | Very thin mouthfeel | Thick mouthfeel, contains fat fullness |
| Acceptibility vs Control | Acceptable for appearance | | Acceptable for appearance | Unacceptable | Unacceptable |

Viscosity Building:

As shown in the above table, the dressing with inulin of the invention was only slightly thicker than the Control but still smooth and pourable. It performed better than the dressings with inulins from the comparative examples for visual consistency, forming a smooth thickened pourable dressing typical of Ranch. The dressing with Cargill Oliggo-Fiber™LC/HT Inulin was closest in consistency to the inventive inulin and to the control but had a slightly thinner consistency. The Orafti Raftiline® HP showed a much thicker consistency more similar to a cream cheese and the dressing with Cargill Oliggo-Fiber™F-97 was much thinner versus the Control and separated after overnight storage.

Fat Replacement & Emulsification:

The dressing with inulin of the invention performed comparable to Cargill Oliggo-Fiber™LC/HT and Orafti Raftiline® HP in emulsification capability and superior to the dressing with Cargill Oliggo-Fiber™F-97 which separated upon overnight storage.

b) White Bread

TABLE 13

| | Inulin (Source) | | | | |
|---|---|---|---|---|---|
| | Inulin according to invention from Artichoke | — (control) | Cargill Oliggo-Fiber™ LC/HT (Chicory) | Cargill Oliggo-Fiber™ F-97 (Chicory) | Orafti Raftiline ® HP (Chicory) |
| mean DPw | 56 | | >20 | 70% is <10 | 25 |
| Mono & Disaccharides | <0.5% | | 1.0% | 3.0% | |
| Moisture Content | 5.40% | | 4.00% | 5.00% | 3.00% |
| Organoleptic Attributes: | | | | | |
| Appearance | Similar to control, more even crumb, slightly denser | Typical bread; good browning and rise, eneven crumb | Similar to control | No rise, Crumbly crumb | Similar to control, coarser crumb |
| Aroma | Similar to control | Typical | Similar to control | Similar to control | Similar to control |
| Acceptibility vs Control | Acceptable appearance | | Acceptable | Unacceptable | Acceptable |
| Qualititative Specifications (baked bread): | | | | | |
| Moisture Content | 32.34% | 33.60% | 31.98% | 31.85% | 32.93% |
| Fat Content | 6.79% | 6.57% | 6.68% | 6.87% | 6.51% |
| Water Activity | 0.910 | 0.890 | 0.907 | 0.906 | 0.898 |
| Crumb Structure (visual) | 0.5-2.0 mm | 0.5-3.0 mm | 1.0-2.0 mm | 0.5-2.0 mm | 0.5-2.0 mm |
| Ease of use: | | | | | |
| Handling | Powdery | | A little dusty | A little dusty | A little dusty |
| Mixing | No issues | | No issues | No issues | No issues |
| Solubility/Dispersibility | Bound up dough | | Wet but smooth dough | Very wet batter | Wet but smooth dough |
| Baking | No issues | | | No rise | |

Inulin of the invention bound more water and formed a firmer dough than the control and competitive inulins. Therefore, the dough resulting from inulin of the invention had a higher binding capacity yielding a tighter and firmer dough resulting in a more even crumb.

Dough with Inulin of the invention baked nicely with good height and color versus the control. The Cargill Oliggo-Fiber™LC/HT dough and bread was similar to the Control. The Orafti Raftiline® HP dough was similar to the Control however the baked bread had a coarser but more even crumb. The Cargill Oliggo-Fiber™F-97 did not have enough binding properties resulting in a dough which did not rise or bake well.

Inulin of the invention gave the best even crumb appearance and a denser texture. The Control and Cargill Oliggo-Fiber™ LC/HT had uneven crumb appearance, the Orafti Raftiline® HP dough had coarse crumb appearance and the Cargill Oliggo-Fiber™F-97 had a crumbly crumb appearance.

In result, inulin of the invention was preferred over the competitive inulins for appearance and crumb delivering.

The invention claimed is:

1. A food comprising an inulin having an average degree of polymerization $DP_w$ of between 54 and 61.

2. The food of claim 1, wherein said food is dairy, yogurts, ice creams, dairy based smoothies, dairy toppings, puddings, milk shakes, custards, cheeses, nutritional bars, energy bars, breakfast bars, confection, bakery, crackers, cookies, biscuits, grain chips, trail mix, iced tea mix, fruit juice smoothies, weight management drinks, ready to drink beverages, sports drinks, endurance drinks, supplement powdered drink mixes, infant and baby formula, calcium fortified orange juice, bread, croissants, cereals, pastas, bread spreads, sugar free candies and chocolates, calcium candy chews, meat products, mayonnaise, salad dressings, nut butters, frozen entrees, sauces, soups or ready meals.

3. The food of claim 1, wherein said food is an extrusion product.

4. The food of claim 1, wherein said food is present in amount effective to modify or modulate the bacterial flora composition in the colon of humans, mammals or other vertebrates.

5. The food of claim 4, wherein said food is present in amount effective to modify or modulate the distal portion of the colon.

6. The food of claim 1, wherein said food is present in amount effective to modify or modulate the fermentation pattern of inulin in the colon of humans, mammals or other vertebrates.

7. The food of claim 6, wherein said food is present in amount effective to modify or modulate the distal portion of the colon.

8. The food of claim 1, wherein said food is present in amount effective to have a prebiotic action and/or a bifidogenicity.

9. The food of claim 1, wherein the inulin has an average degree of polymerization $DP_w$ of between 55 and 60.

10. The food of claim 9, wherein the inulin has an average degree of polymerization $DP_w$ of between 56 and 57.

11. The food of claim 1, wherein the glucose content is less than 2%.

12. The food of claim 11, wherein the glucose content is less than 1%.

13. The food of claim 1, wherein the fructose content is less than 2.5%.

14. The food of claim 13, wherein the fructose content is less than 1.5%.

15. The food of claim 1, wherein the content of fructooligosaccharides with a degree of polymerization (DP) of from 3 to 10 is less than 3%.

16. The food of claim 15, wherein the content of fructooligosaccharides with a DP of from 3 to 10 is less than 1.5%.

17. The food of claim 16, wherein the content of fructooligosaccharides with a DP of from 3 to 10 is less than 0.7%.

18. The food of claim 1, wherein at a concentration of 30% w/v of inulin in water at 90° C. the viscosity is 300-1000 mPas at a shear rate of $20s^{-1}$.

19. A dietary supplement comprising an inulin having an average degree of polymerization $DP_w$ of between 54 and 61.

* * * * *